(12) United States Patent
Kim et al.

(10) Patent No.: US 11,867,703 B2
(45) Date of Patent: Jan. 9, 2024

(54) METHOD OF PRODUCING TEST STRIPS FOR COLORIMETRIC DETERMINATION OF CALCIUM LEVEL IN BIOLOGICAL FLUID USING CA-OCPC COMPLEX

(71) Applicant: CHUNDO PHARM CO., LTD, Chuncheon-si (KR)

(72) Inventors: Sung Jin Kim, Seoul (KR); Abeje Abebayehu Silte, Chuncheon-si (KR)

(73) Assignee: CHUNDO PHARM CO., LTD, Chuncheon-si (KR)

( * ) Notice: Subject to any disclaimer, the term of this patent is extended or adjusted under 35 U.S.C. 154(b) by 224 days.

(21) Appl. No.: 17/535,482

(22) Filed: Nov. 24, 2021

(65) Prior Publication Data

US 2022/0091141 A1    Mar. 24, 2022

Related U.S. Application Data

(63) Continuation-in-part of application No. 17/103,950, filed on Nov. 25, 2020, now Pat. No. 11,313,853.

(30) Foreign Application Priority Data

Sep. 23, 2020   (KR) .................. 10-2020-0122768

(51) Int. Cl.
*G01N 33/84*   (2006.01)

(52) U.S. Cl.
CPC .................. *G01N 33/84* (2013.01)

(58) Field of Classification Search
CPC ...... G01N 33/523; G01N 33/84; G01N 21/78; G01N 2021/7759
See application file for complete search history.

(56) References Cited

U.S. PATENT DOCUMENTS

2012/0275969 A1   11/2012   Nakamura

FOREIGN PATENT DOCUMENTS

| EP | 0 475 045 A1 | 3/1992 |
|---|---|---|
| KR | 10-2007-0073682 A | 7/2007 |
| KR | 10-2010-0111872 A | 10/2010 |
| KR | 10-2012-0135291 A | 12/2012 |

*Primary Examiner* — Jennifer Wecker
*Assistant Examiner* — Kathryn Elizabeth Limbaugh
(74) *Attorney, Agent, or Firm* — Sughrue Mion, PLLC

(57) ABSTRACT

Disclosed is a method of producing a test strip for detecting a calcium level in a body fluid test sample obtained from a biological subject such as a human or animal. Also disclosed is a test strip that is useful for determining the concentration of calcium in a human or animal body fluid test sample based on a colorimetric change, and thus provides early detection of osteoporosis by monitoring the calcium excretion rate in an easy and inexpensive manner.

11 Claims, 5 Drawing Sheets

Calcium level measured by dry test strip

Magnesium Interference

| Calcium Concentration | Interferent Concentration (mg/dL) | | |
|---|---|---|---|
| | 2 | 5 | 10 |
| Low (1mg/dL) | | | |
| High (50mg/dL) | | | |

FIG. 5

Bilirubin interference

| Calcium Concentration | Interferent Concentration (mg/dL) | | |
|---|---|---|---|
| | 30 | 35 | 40 |
| Low (1mg/dL) | | | |
| High (50mg/dL) | | | |

FIG. 6

Hemoglobin interference

| Calcium Concentration | Interferent Concentration (mg/dL) | | |
|---|---|---|---|
| | 40 | 45 | 50 |
| Low (1mg/dL) | | | |
| High (50mg/dL) | | | |

FIG. 7

Phosphate interference

| Calcium Concentration | Interferent Concentration (mg/dL) | | |
|---|---|---|---|
| | 40 | 45 | 50 |
| Low (1mg/dL) | | | |
| High (50mg/dL) | | | |

FIG. 8

Ascorbic acid interference

| Calcium Concentration | Interferent Concentration (mg/dL) | | |
|---|---|---|---|
| | 50 | 75 | 100 |
| Low (1mg/dL) | | | |
| High (50mg/dL) | | | |

METHOD OF PRODUCING TEST STRIPS FOR COLORIMETRIC DETERMINATION OF CALCIUM LEVEL IN BIOLOGICAL FLUID USING CA-OCPC COMPLEX

CROSS-REFERENCE TO RELATED APPLICATIONS

This application is a Continuation-in-Part of U.S. application Ser. No. 17/103,950 filed Nov. 25, 2020, which claims priority from Korean Patent Application No. 10-2020-0122768 filed Sep. 23, 2020, the disclosures of all of which are incorporated herein by reference in their respective entireties.

BACKGROUND OF THE INVENTION

Field of the Invention

The present invention relates to a method of producing a test strip for detecting a calcium level in a body fluid test sample obtained from a biological subject such as a human or animal based on a colorimetric change.

Description of the Related Art

Biological fluids such as blood serum, urine, and saliva contain a wealth of biochemical markers that have been excreted from the body. Accordingly, such biological fluids may be assayed in order to determine the concentrations of specific metabolites or electrolytes, and variation in the concentrations of metabolites or electrolytes is indicative of various medical conditions.

Calcium ions play a key role in muscle contraction, nerve signal transmission, formation of strong bones and teeth, blood clotting, heartbeat regulation, intercellular balance, and the like. The amount of calcium ions in the blood is strictly regulated in a manner similar to that for a variety of metal ions, enzymes and hormones. Great variation in blood calcium levels causes cancer, muscle dysfunction, and various other diseases.

Calcium concentration as the result of a disease may be either higher or lower than that in a normal state. Variation in blood calcium levels may be due to parathyroid diseases, bone diseases, incomplete absorption of calcium through the intestine, kidney diseases, multiple myeloma, and various other abnormalities. Therefore, it is very important to measure the amount of calcium in body fluids in an easy, inexpensive and fast manner.

Calcium level measurement is used in the diagnosis and treatment of parathyroid diseases, a variety of bone diseases, and chronic renal diseases. Although 99% or more of body calcium exists in the bones and teeth, blood calcium is of the greatest clinical concern. The bones act as a reservoir to maintain relative constancy of calcium by releasing calcium if needed to prevent hypocalcemia and taking up calcium to prevent hypercalcemia, which is a condition in which the calcium level in blood is excessively high. Uptake and release of calcium from the bones is under the control of the parathyroid hormone.

Hypocalcemia refers to a condition in which the level of calcium in the blood is low. Hypocalcemia may be caused by administration of drugs, such as diuretics or therapeutic agents, or the progression of diseases, such as renal failure or hypotension and administration of therapeutic agents for treatment therefor. Insufficient dietary calcium generally does not cause hypocalcemia. The reason for this is that the human body can extract calcium from the bones as needed to maintain normal blood calcium levels.

However, continuous dietary calcium deficiency may eventually lead to osteomalacia and osteoporosis. For this reason, appropriate treatment should be received in order to reduce the risk of serious complications from calcium deficiency. Long-term calcium deficiency may lead to osteoporosis, in which the bones are weakened and the risk of fracture increases. Osteoporosis is characterized by decreased bone density and mass. Osteoporotic hip fractures cause significant morbidity and mortality in the aged population.

Osteoporosis is becoming increasingly common in the aging population; as many as 60% of women and 30% of men over the age of sixty years suffer at least one osteoporotic fracture. The increasing prevalence of this disease, particularly among women, and the fact that further bone deterioration can be prevented by treatment if identified at an early stage, has resulted in research into the early detection or prediction of osteoporosis in perimenopausal women, which is of major scientific importance.

Osteoporosis is completely preventable but only partially treatable. For this reason, early detection of osteoporosis is crucial in order to prevent further bone deterioration. The results of research have shown that many women lose bone after menopause at a rate greater than 3% and up to 7% per year. Further, it has been reported that in the majority of cases exhibiting osteoporosis symptoms, 20% to 40% of bone mineral content is already lost before diagnosis.

Meanwhile, hypercalcemia refers to a condition in which the calcium level in the blood is higher than normal. Hypercalcemia usually results from overactive parathyroid glands. Hypercalcemia occurs most commonly in breast cancer, lymphoma, prostate cancer, thyroid cancer, lung cancer, myeloma, and colon cancer. Hypercalcemia may be caused by secretion of parathyroid-hormone-related peptides due to tumors or by the release of calcium resulting directly from invasion of bone tissue. Symptoms of hypercalcemia include anorexia, nausea, vomiting, constipation, abdominal pain, lethargy, depression, confusion, polyurea, pains, and the like.

Highly specialized methods such as bone densitometry may assist in predicting the likelihood of bone fractures. However, such methods are generally not performed due to the high cost thereof. Therefore, when this test is actually performed, in the majority of cases, the patient has already lost significant quantities of bone minerals. Ultimately, such an expensive test is not helpful in the practical diagnosis of perimenopausal women who are likely to become osteoporotic.

Successful detection of the onset of osteoporosis can be realized by measuring calcium concentrations in sera or urine. As it is commonly known that the amount of calcium in the urine directly relates to the rate of bone loss in menopausal adults, it is well established that urinary calcium measurement is an early indicator of rapid bone loss and is useful as an early diagnosis means for predicting osteoporosis.

RELATED ART

Patent Literature

Korean Patent Laid-open Publication No. 10-2012-0135291 (publication date: Dec. 12, 2012) discloses a reagent for detecting calcium and a method of detecting calcium using the reagent.

SUMMARY OF THE INVENTION

Therefore, the present invention has been made in view of the above problems, and it is an object of the present invention to provide a test strip for detecting the concentration of calcium in a human or animal body fluid test sample based on a color change.

In accordance with the present invention, the above and other objects can be accomplished by the provision of a method of producing a test strip for detecting a calcium concentration in a sample obtained from a biological subject, the method including impregnating paper with a primary reagent, followed by drying (a), and impregnating the paper dried in step (a) with a secondary reagent, followed by drying (b), wherein the primary reagent is prepared by adding o-cresolphthalein complexone (OCPC), 8-hydroxyquinoline, sodium lauryl sulphate (SDS) and polyvinylpyrrolidone (PVP) to distilled water, followed by mixing and further adding an organic acid thereto, and the secondary reagent is prepared by adding N-cyclohexyl-3-aminopropanesulfonic acid and N-methyl-D-glucamine to distilled water, followed by mixing and further adding Triton X-100 and triethylamine borate thereto.

The paper is preferably Whatman paper.

The drying of step (a) or drying of step (b) is preferably carried out at 55 to 65° C. for 10 to 20 minutes.

The biological subject is preferably a human or an animal.

In accordance with another aspect of the present invention, provided is a method of producing a test strip for detecting a calcium concentration in a sample obtained from a biological subject, the method including impregnating paper with a mixed solution of a primary reagent and a secondary reagent, followed by drying, wherein the first reagent is prepared by dissolving o-cresolphthalein complexone (OCPC), sodium lauryl sulphate (SDS), polyvinylpyrrolidone (PVP), and a compound for selectively masking magnesium in an organic solvent, followed by further adding an organic acid thereto, and the second reagent is prepared by adding a pH buffer for adjusting a pH to 10.0 to 11.0 during the reaction between calcium in the sample and OCPC of the primary reagent, 2,7-bis(2-arsonophenylazo) chromotropic acid and Triton x-100 to distilled water.

The paper is preferably Whatman paper.

The drying is preferably performed at 55 to 65° C. for 10 to 20 minutes.

The compound for selectively masking magnesium is preferably 8-hydroxyquinoline.

The organic acid is preferably citric acid.

The pH buffer for adjusting a pH to 10.0 to 11.0 during the reaction between calcium in the sample and OCPC of the primary reagent is preferably a mixed solution of N-cyclohexyl-3-aminopropanesulfonic acid, N-methyl-D-glucamine, and triethylamine borate.

The biological subject is preferably a human or an animal.

BRIEF DESCRIPTION OF THE DRAWINGS

The above and other objects, features, and other advantages of the present invention will be more clearly understood from the following detailed description taken in conjunction with the accompanying drawings, in which:

FIG. 5 illustrates the result of bilirubin interference evaluation of the test strip produced by the method according to another aspect of the present invention;

FIG. 6 illustrates the result of hemoglobin interference evaluation of the test strip produced by the method according to another aspect of the present invention;

FIG. 7 illustrates the result of phosphate interference evaluation of the test strip produced by the method according to another aspect of the present invention; and FIG. 8 illustrates the result of ascorbic acid interference evaluation of the test strip produced by the method according to another aspect of the present invention.

DETAILED DESCRIPTION OF THE INVENTION

Figure 1:
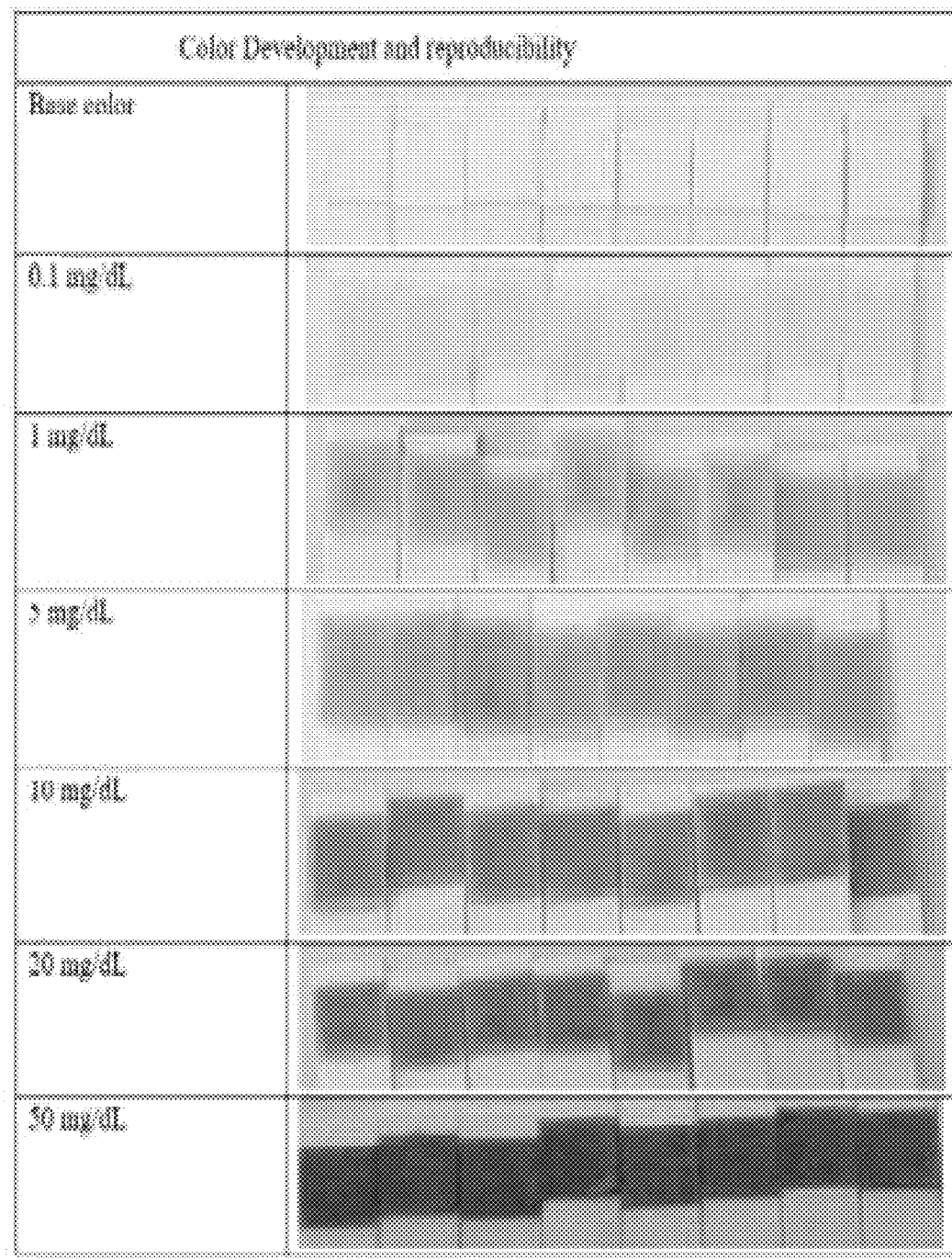
FIG. 1 illustrates the result of testing of the calcium concentration, which is controlled in advance, in order to determine the effectiveness of a test strip produced by the method according to one aspect of the present invention.

A recently known method for colorimetric detection of calcium is to detect a colored form of calcium, obtained by chelating calcium with OCPC in the presence of an alkaline buffer, and is most widely used. However, the method has a problem in that a large measurement error occurs because the pH of the prepared reagent itself is low, and it is often difficult to control the pH. In addition, the test strip produced according to the method has a problem of causing detection of false positives due to the formation of a complex of magnesium with OCPC in a buffer of pH 10.0 to 11.0. However, the method using the test strip advantageously involves an immediate color change and provides a routine calcium excretion test, and is thus still widely used.

The present invention provides a test strip that has a smaller error when measuring the calcium concentration by the OCPC method using two solutions, namely a primary reagent and a secondary reagent, and drying the primary reagent and then immersing the test paper in the secondary reagent. A sample obtained from a biological subject (a living organism) is used and the biological subject is preferably a human or an animal. Also, the sample obtained from the biological subject is preferably urine.

The method of producing a test strip according to a first aspect of the present invention includes two steps: immersing paper (preferably Whatman paper) in a calcium dye reagent (primary reagent), followed by drying, and subsequently immersing the paper in a buffer solution (secondary reagent), followed by drying.

The primary reagent, which is a calcium dye reagent, is prepared by adding o-cresolphthalein complexone (OCPC), 8-hydroxyquinoline, sodium lauryl sulphate (SDS), and polyvinylpyrrolidone (PVP) to distilled water, followed by mixing and then adding citric acid thereto.

OCPC (o-cresolphthalein complexone) is a dye that reacts with calcium to form a complex. The following Formula 1 represents the structure of o-cresolphthalein complexone.

[Formula 1]

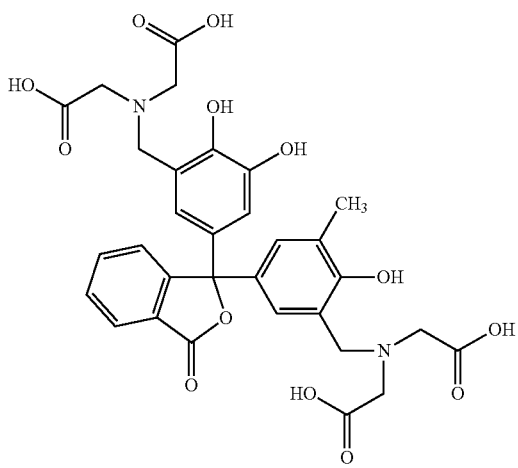

As shown in the following Reaction scheme, OCPC reacts with calcium at pH 10 to 11 to develop violet.

[Reaction Scheme 1]

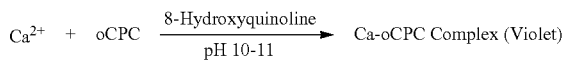

8-hydroxyquinoline is an ingredient used to selectively mask magnesium, which causes false positives. In addition, 8-quinolinol sulphate or N-benzoyl-N-phenyl-hydroxylamine may be used. At a pH of 7 to 8, the OCPC dye may also react with magnesium. As the pH increases, the reactivity therebetween deteriorates. However, a masking ingredient can block the interference of magnesium. For this reason, the use of an ingredient for selectively masking magnesium is recommended. Magnesium, which is an element that acts as interference when measuring calcium, can be effectively removed by using the high pH (10-11) and the magnesium coupling agent (8-hydroxyquinoline) suggested in the present invention.

SDS is a nonionic surfactant, and does not undergo hydrolysis in an aqueous acid or alkaline solution. The surfactant reagents including Triton X-100, used as secondary reagents, improve the color and concentration of dyes that have undergone color changes. The surfactant reagents also improve the level of color dispersion throughout the reactive pad, the smoothness (softness) of the test strip surface, the rate of color change and the like. In addition, these surfactants were found to improve the brightness of changing colors, as well as the absorbency of the test strip.

PVP was used as a stabilizer.

The organic acid was used as a pH buffer. The organic acid that may be used as the pH buffer may be selected from the group consisting of citric acid, malonic acid, phosphoric acid, malic acid, succinic acid, phthalic acid, glutaric acid, and the like. The organic acid is preferably citric acid.

Meanwhile, the secondary reagent, which is a buffer solution, is prepared by adding N-cyclohexyl-3-aminopropanesulfonic acid and N-methyl-D-glucamine to distilled water, followed by mixing and then adding Triton X-100 and triethylamine borate thereto.

The secondary reagent acts as a pH buffer to adjust the pH of the environment to react calcium with OCPC to 10.0 to 11.0. The buffer should maintain the pH of the sample in the range of 10 to 11, and at such a high pH level, OCPC reacts with calcium ions, but does not actively react with magnesium.

A buffer suitable for the reagent may be selected from amino methyl propanol (AMP), 3-(cyclohexylamino)-1-propanesulfonic acid (CAPS), N-methyl-D-glucamine, carbonate buffers, sodium borate, and combinations thereof. However, N-cyclohexyl-3-aminopropanesulfonic acid and N-methyl-D-glucamine are preferably used by adjusting triethylamine borate. In this case, N-cyclohexyl-3-aminopropanesulfonic acid and N-methyl-D-glucamine are mixed at a ratio of 9:1. It is important that the pH buffer does not react with calcium ions in competition with the dye. The pH buffer containing this ingredient does not compete with the dye for calcium ions. In this case, the pH buffer concentration is preferably about 0.1M to about 0.5M.

Meanwhile, the ingredient Triton X-100 is a surfactant, and the action thereof has already been described above.

Meanwhile, in a second aspect, the present invention provides a method for producing a test strip. The method of producing a test strip according to the second aspect includes impregnating paper with a mixed solution of a primary reagent and a secondary reagent, followed by drying. The first reagent is prepared by dissolving o-cresolphthalein complexone (OCPC), sodium lauryl sulphate (SDS), polyvinylpyrrolidone (PVP), and a compound for selectively masking magnesium in an organic solvent and then further adding an organic acid thereto. The second reagent is prepared by adding a pH buffer for adjusting a pH to 10.0 to 11.0 during the reaction between calcium in the sample and OCPC of the primary reagent, 2,7-bis(2-arsonophenylazo) chromotropic acid, and Triton x-100 to distilled water.

The biggest difference between the method of producing the test strip according to the first aspect and the method of producing the test strip according to the second aspect pertains to whether or not 2,7-bis(2-arsonophenylazo) chromotropic acid (Formula 2 below) is added. 2,7-bis(2-arsonophenylazo)chromotropic acid improves the accuracy of the test strip by extending the pH range within which OCPC reacts with calcium to form a complex. Therefore, the test strip according to the production method of the present invention responds sensitively to calcium even when tested using a liquid (urine, saliva, etc.) obtained from a biological subject as a sample, resulting in a color change in a calcium-concentration-dependent manner. Then, the calcium concentration can be accurately measured by visual comparison using a colorimetric table etc. or calculation of colorimetric RGB values using an analyzer.

[Formula 2]

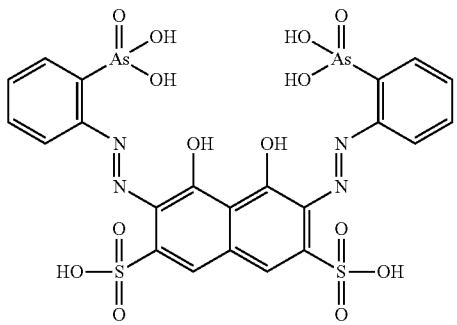

Structure of 2,7-bis(2-arsonophenylazo) chromotropic acid

As can be seen from the following example, the test strip produced by the method according to the second aspect reflects the calcium concentration very accurately. In addition, it can be seen that false positive reactions due to magnesium, bilirubin, hemoglobin and phosphate are inhibited and thus the accuracy is very high.

Meanwhile, in the method of producing the test strip according to the second aspect, the drying is preferably performed at 55 to 65° C. for 10 to 20 minutes. This temperature range can shorten the drying time and does not affect the reagents or paper used in the present invention. In addition, this time range is suitable for drying depending on the temperature.

Meanwhile, in the method for producing the test strip of the second aspect, the compound for selectively masking magnesium may be, for example, 8-hydroxyquinoline, 8-quinolinol sulphate, or N-benzoyl-N-phenyl-hydroxylamine, preferably 8-hydroxyquinoline. As can be seen from the following examples, when 8-hydroxyquinoline was used as an agent for selectively masking magnesium, false positive reactions caused by magnesium were inhibited well.

Meanwhile, in the method of producing the test strip according to the second aspect, the organic acid may be, for example, malonic acid, phosphoric acid, malic acid, citric acid, succinic acid, phthalic acid, or glutaric acid, preferably citric acid. Citric acid contributes to controlling the pH of the environment under which calcium reacts with OCPC.

Meanwhile, in the method for producing the test strip according to the second aspect, the pH buffer for controlling the pH to 10.0 to 11.0 during the reaction between the calcium in the sample and the OCPC of the first reagent may be selected from buffers suitable for the reagent composition and combinations thereof, and is preferably N-cyclohexyl-3-aminopropanesulfonic acid, N-methyl-D-glucamine and triethylamine borate.

N-cyclohexyl-3-aminopropanesulfonic acid and N-methyl-D-glucamine are suitable for the control of triethylamine borate, and a mixture of N-cyclohexyl-3-aminopropanesulfonic acid and N-methyl-D-glucamine in a weight ratio of 9:1 can reduce errors in the test strip since the buffer does not compete with the dye for calcium ions.

Meanwhile, in the method of producing the test strip according to the second aspect, the sodium lauryl sulphate (SDS), Triton x-100, and PVP were used to obtain other desirable properties of the test strip.

SDS (sodium lauryl sulphate) and Triton x-100 are nonionic surfactants that improve the color tone of dyes that change color, the level of color dispersion of the test strip, the smoothness of the surface of the test strip, the color change rate of the test strip, and the absorbance of the test strip. In addition, Triton x-100 (p-isooctyl phenyl ether) also functions as a diffusion agent to prevent the reagent from coagulating. PVP was used as a stabilizer.

Hereinafter, the present invention will be described in more detail with reference to the following examples. The scope of the present invention is not limited to the examples, and encompasses modifications of the technical concept equivalent thereto.

Example 1: Production of Test Strip Using Method According to One Aspect of Present Invention The method of producing the test strip capable of detecting the calcium concentration in a biological sample according to the present invention was accomplished by sequentially impregnating paper with a primary reagent and a secondary reagent and drying the paper, prior to performing processes associated with the secondary reagent. That is, the paper (Whatman paper) was immersed in the primary reagent described below and then dried, and the dried paper was immersed in the secondary reagent and then dried to produce the test strip according to the present invention. At this time, drying was performed at 60° C. for about 15 minutes.

1) Preparation of Primary Reagent 0.5 g of OCPC (ingredient for determining calcium content), 5 g of 8-hydroxyquinoline (reagent for selectively masking magnesium), 2.5 g of sodium lauryl sulphate (nonionic surfactant), and 3.5 g of PVP (stabilizer) were mixed with distilled water, used as a solvent. At this time, the pH was adjusted to 10 to 11 by adding citric acid thereto.

2) Preparation of Secondary Reagent 3.3 g of N-cyclohexyl-3-aminopropanesulfonic acid (pH buffer) and 0.37 g of N-methyl-D-glucamine (pH buffer) were mixed with distilled water, used as a solvent. The resulting solution was further mixed with 0.2 g of Triton X-100 (surfactant) and 4 g of triethylamine borate (pH buffer). In the last step, distilled water was added such that the final volume was adjusted to 1 L.

Example 2: Test of Effectiveness of Test Strip According to Example 1

Figure 2:
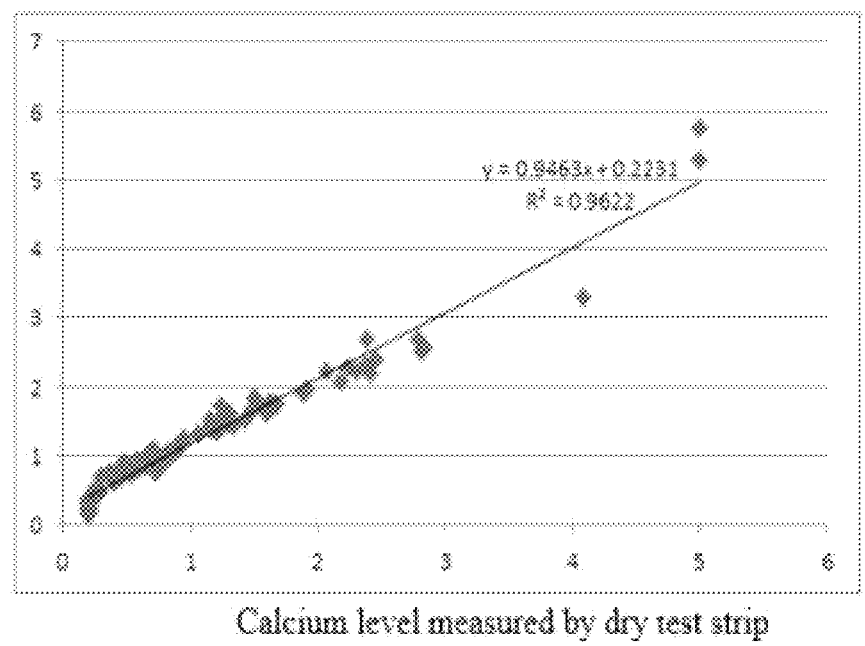
FIG. 2 illustrates the calcium concentration measured using an electrolyte measuring device and calcium concentration measured using the test strip of the present invention in order to determine the effectiveness of the test strip produced by the method according to one aspect of the present invention.

The effectiveness of the test strip according to the present invention produced in Example 1 was tested (FIGS. 1 and 2). FIG. 1 shows the result of testing of a pre-adjusted calcium concentration in order to determine the measurement effectiveness of the test strip of the present invention. As can be seen from FIG. 1, a colorimetric assay depending on calcium concentration was successful. FIG. 2 shows the calcium concentration obtained by the colorimetric assay (determined based on the colorimetric change) and the calcium concentration measured using an electrolyte analyzer (Roche AVL 9180), which supports the measurement accuracy of the test strip according to the present invention.

Example 3: Production of Test Strip Using Method of Second Aspect of Present Invention The method for producing the test strip according to the second aspect of the present invention capable of measuring the calcium concentration in a biological sample includes impregnating paper (Whatman paper) with a mixed solution of a primary reagent and a secondary reagent, and then drying the paper. At this time, drying was performed at 60° C. for about 15 minutes.

1) Preparation of Primary Reagent

The primary reagent was prepared by mixing 500 ml of 50% (v/v) ethanol as a solvent with 0.8 g of OCPC (o-cresolphthalein complexone), 4.5 g of SDS (sodium lauryl sulphate), 6.5 g of PVP40 (polyvinylpyrrolidone40), and 7.5 g of 8-hydroxyquinoline, and then adding 0.05 mol/L of citric acid-sodium citrate buffer thereto to adjust the final volume to 1 L.

2) Preparation of Secondary Reagent

The secondary reagent was prepared by mixing 3.3 g of N-cyclohexyl-3-aminopropane sulfonic acid, 0.67 g of N-methyl-D-glucamine, 8 g of triethylamine borate, 0.18 g of 2,7-bis(2-arsonophenylazo) chromotropic acid, and 0.5 g of Triton x-100 with distilled water as a solvent and then further adding distilled water thereto to adjust the final volume to 1 L.

Example 4: Test of Effectiveness of Test Strip According to Example 3

Figures 3, 4:
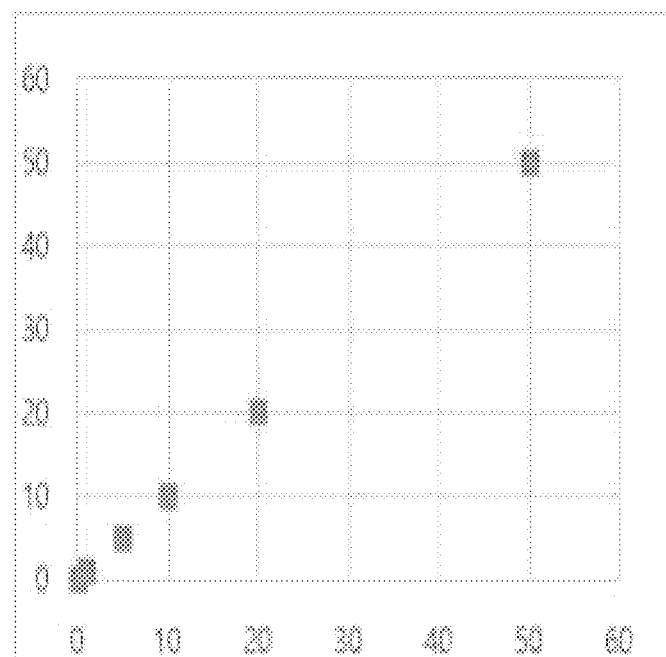
FIG. 3 illustrates the result of testing of the calcium concentration, which is controlled in advance, and the calcium concentration measured through a colorimetric table in order to determine the effectiveness of the test strip produced by the method according to another aspect of the present invention.
FIG. 4 illustrates the result of magnesium interference evaluation of the test strip produced by the method according to another aspect of the present invention.

The effectiveness of the test strip of the present invention produced in Example 3 was tested. In order to determine the effectiveness, the pre-adjusted calcium concentration was tested, and the calcium concentration was measured through a colorimetric table (FIG. 3). It can be seen from the results of FIG. 3 that the test strip of the present invention exhibited very good accuracy.

Example 5: Test of Interference of Test Strip According to Example 3

The potential interference of the test strip of the present invention produced in Example 3 was determined. For this purpose, each of magnesium, bilirubin, hemoglobin, phosphate and ascorbic acid was added to a calcium solution to prepare a mixed solution, the test strip of the present invention was added to the prepared mixed solution, and then a color change was observed. The maximum concentration of each solution was 10 mg/dL for magnesium, 40 mg/dL for bilirubin, 50 mg/dL for hemoglobin, 50 mg/dL for phosphate, and 100 mg/dL for ascorbic acid. The maximum concentration of each solution was determined in consideration of the physiological concentration range of the biological body fluid.

FIG. 4 illustrates the result of magnesium interference evaluation of the test strip according to Example 3.

FIG. 5 illustrates the result of bilirubin interference evaluation of the test strip according to Example 3.

FIG. 6 illustrates the result of hemoglobin interference evaluation of the test strip according to Example 3.

FIG. 7 illustrates the result of phosphate interference evaluation of the test strip according to Example 3.

FIG. 8 illustrates the result of ascorbic acid interference evaluation of the test strip according to Example 3.

It can be seen from the evaluation results that the test strip of the present invention according to Example 3 exhibits very little interference. The test strip exhibiting the highest interference had a color change corresponding to about 0.5 mg/dl of calcium, which is within 5% of the normal calcium concentration and is thus not considered to be a significant interference result.

As is apparent from the foregoing, the present invention provides a test strip that is useful for determining the concentration of calcium in a human or animal body fluid test sample based on a colorimetric change, and thus provides early detection of osteoporosis by monitoring the calcium excretion rate in an easy and inexpensive manner.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of producing a test strip for detecting a calcium concentration in a sample obtained from a biological subject, the method comprising:
    impregnating paper with a primary reagent, followed by drying (a); and
    impregnating the paper dried in step (a) with a secondary reagent, followed by drying (b),
    wherein the primary reagent is prepared by adding o-cresolphthalein complexone (OCPC), 8-hydroxyquinoline, sodium lauryl sulphate (SDS), and polyvinylpyrrolidone (PVP) to distilled water, followed by mixing and further adding an organic acid thereto, and
    the secondary reagent is prepared by adding N-cyclohexyl-3-aminopropanesulfonic acid and N-methyl-D-glucamine to distilled water, followed by mixing and further adding Triton X-100 and triethylamine borate thereto.

2. The method according to claim 1, wherein the paper is Whatman paper.

3. The method according to claim 1, wherein the drying of step (a) or the drying of step (b) is carried out at 55 to 65° C. for 10 to 20 minutes.

4. The method according to claim 1, wherein the biological subject is a human or an animal.

5. A method of producing a test strip for detecting a calcium concentration in a sample obtained from a biological subject, the method comprising:
    impregnating paper with a mixed solution of a primary reagent and a secondary reagent, followed by drying,
    wherein the first reagent is prepared by dissolving o-cresolphthalein complexone (OCPC), sodium lauryl sulphate (SDS), polyvinylpyrrolidone (PVP), and a compound for selectively masking magnesium in an organic solvent, followed by further adding an organic acid thereto, and
    the second reagent is prepared by adding a pH buffer for adjusting a pH to 10.0 to 11.0 during the reaction between calcium in the sample and OCPC of the primary reagent, 2,7-bis(2-arsonophenylazo) chromotropic acid, and Triton x-100 to distilled water.

6. The method according to claim 5, wherein the paper is Whatman paper.

7. The method according to claim 5, wherein the drying is performed at 55 to 65° C. for 10 to 20 minutes.

8. The method according to claim 5, wherein the compound for selectively masking magnesium is 8-hydroxyquinoline.

9. The method according to claim 5, wherein the organic acid is citric acid.

10. The method according to claim 5, wherein the pH buffer for adjusting a pH to 10.0 to 11.0 during the reaction between calcium in the sample and OCPC of the primary reagent is a mixed solution of N-cyclohexyl-3-aminopropanesulfonic acid, N-methyl-D-glucamine, and triethylamine borate.

11. The method according to claim 5, wherein the biological subject is a human or an animal.

* * * * *